United States Patent [19]

Gàetani et al.

[11] 4,366,099
[45] Dec. 28, 1982

[54] PROCESS FOR TREATING COSMETIC OILS SO AS TO MODIFY THEIR PROPERTIES AND COSMETIC COMPOSITIONS CONTAINING THESE OILS

[75] Inventors: Quintino Gàetani, Bondy; Christos Papantoniou, Montmorency, both of France

[73] Assignee: Societe Anonyme dite: L'Oreal, Paris, France

[21] Appl. No.: 143,730

[22] Filed: Apr. 25, 1980

[30] Foreign Application Priority Data

May 4, 1979 [FR] France ................ 79 11273

[51] Int. Cl.³ ............................................. C08F 19/14
[52] U.S. Cl. .................... 260/407; 424/64;
525/279; 525/285; 526/258; 526/318;
526/348.7; 525/283; 525/303; 525/296;
525/301; 525/293; 526/320; 526/304; 526/317;
526/307.8; 526/312; 526/307.7
[58] Field of Search ............. 260/407, 23 CP, 23 AR, 260/28 R, 28.5 R; 424/64; 525/279, 285, 326, 327; 526/258, 303, 318, 348.7

[56] References Cited

U.S. PATENT DOCUMENTS

| Re. 30,747 | 9/1981 | Muszik et al. ............. 260/23 AR |
| 2,863,784 | 12/1958 | Hillyer ................... 260/23 AR |
| 3,010,925 | 11/1961 | Lynn ...................... 260/23 AR |
| 3,166,524 | 1/1965 | Schmidle et al. ........... 260/23 CP |
| 3,873,584 | 3/1979 | Burke et al. .............. 260/23 CP |

*Primary Examiner*—John F. Niebling
*Attorney, Agent, or Firm*—Cushman, Darby & Cushman

[57] ABSTRACT

A process for reducing the volatility and improving the emulsifying power of an unsaturated or saturated cosmetic oil comprising heating the cosmetic oil, in the absence of a solvent and under an inert atmosphere, with a homopolymerizable and hydrophilic monomer in the presence of an initiator generating free radicals. The monomer is selected from the group consisting of N-vinylpyrrolidone, 2-hydroxymethyl acrylate, 2-hydroxymethyl methacrylate, acrylamide, methacrylamide, N-hydroxymethyl acrylamide, N-(carboxyhydroxy) methacrylamide, acrylic acid, methacrylic acid, 2-vinylpyridine, 4-vinylpyridine and a monomer having the formula,

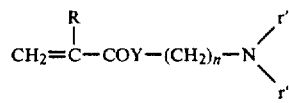

wherein R is hydrogen or methyl, Y is O or NH, r' is methyl or ethyl and n is 2 or 3. The resulting modified oil is then purified to remove any insoluble nongrafted homopolymer.

14 Claims, No Drawings

PROCESS FOR TREATING COSMETIC OILS SO AS TO MODIFY THEIR PROPERTIES AND COSMETIC COMPOSITIONS CONTAINING THESE OILS

This invention has for its object a process for treating cosmetic oils to modify their properties, the oils obtained by this process and the cosmetic compositions containing them.

Numerous cosmetic compositions contain in a variable proportion an oil whose role can be very varied.

Of the various properties common to the group of cosmetic oils whether natural (vegetable, animal or mineral) or synthetic it can be noted that they are liquid, exhibit a slight volatility at ambient temperature and are insoluble in water.

This insolubility in water makes it possible to obtain the "water-in-oil" or "oil-in-water" type emulsions if the oil phase constitutes either the continuous phase or the dispersed phase of the emulsion.

Further, oils have a smooth feel and their lubricating properties generally facilitate application and spreading on the skin, leaving a hydrophobic film on its surface.

This latter property is linked to the emollient character of cosmetic oils. The emollient action, which is reflected by improvement or maintenance of the suppleness of the skin, can be explained by the formation of this hydrophobic film maintaining the water content of the skin by preventing it from evaporating even under conditions of atmospheric dryness or cold.

Moreover, the oils constitute particularly choice solvents and thus are used as vehicles for various active substances intended to come in contact with the skin or hair.

From these main properties can be seen the importance of oils in cosmetic compositions whether these latter are in the form of creams, i.e., emulsions whose oils constitute the fatty phase or in the form of lipstick, rouge, foundation, etc., whose oils constitute an important part of the fatty body in association with waxes.

Further, oils go into types of cosmetic compositions other than those intended for treating skin and particularly compositions for the hair and nails and bath compositions.

For the cosmetician, oils therefore are an essential ingredient whose choice will depend on the nature of the composition sought and the desired cosmetic properties.

With the exception of synthetic oils whose inventory constantly grows, natural oils, such as vegetable, animal and mineral oils, used by cosmeticians are about the same as those used for many decades.

Despite the progress of organic synthesis, it has not been possible to develop synthetic oils able totally to replace natural oils becauses these latter undeniably offer properties particularly desired in cosmetics. However, despite these advantages, these natural oils are not without certain drawbacks that at times limit their use. Of these there can be mentioned in particular the greasy or at times slightly sticky or tacky feel, an insufficient emollient action, deposit of a film with a shiny appearance generally considered unesthetic and indicating a lack of penetration and finally a weak emulsifying power.

Various processes have already been proposed to improve the properties of natural oils of which the main process consists in increasing the purity of oils by various stages of purification to eliminate certain substances.

Further, it has been suggested to modify certain oils containing unsaturated compounds by Diels-Alder type condensation reactions with a particularly reactive unsaturated compound such as maleic anhydride. The oils thus treated were found to exhibit new, particularly interesting properties especially favoring the formation of dispersions in water after salification.

This type of condensation, however, is possible only to the extent that the oils contain conjugated diene compounds or those able to lead to such compounds by isomerization.

These oils, thus modified, have found an application in very diverse fields and more particularly in maintenance products such as polishes, waxes, and in the textile, leather, paper and rubber industries.

Further, it has also been proposed to modify certain natural drying oils by polymerization reaction in the presence of cyclopentadiene and an unsaturated monomer to increase the degree of unsaturation of the oils and thus make possible the rapid formation of films in such fields as paints and varnishes.

To improve the properties of oils generally used in cosmetics, the applicant company has found that excellent results can be obtained when natural oils but also synthetic oils are subjected to a grafting process with certain monomers which must have both a good hydrophily and be easily homopolymerizable.

By this new process causing certain classes of monomers to intervene, the oils thus modified, whether natural or synthetic, prove to have new properties that the untreated oils do not have or have in only a slight degree.

In particular, this process makes it possible to reduce the volatility of the oils and improve their emulsifying power so that possibly it is possible to do without emulsifying agents in the formation of emulsions, without thereby harming their stability in time.

Further, it has been found that these modified oils exhibit good emollient properties to make possible the application of compositions to the skin without leaving a shiny film.

This invention has for its object a process for modifying the properties of cosmetic oils by grafting, a process consisting of heating, under an inert atmosphere, a natural or synthetic cosmetic oil in the presence of an initiator generating free radicals and a homopolymerizable hydrophilic monomer taken from the group made up of N-vinylpyrrolidone, 2-hydroxyethyl acrylate or methacrylate, acrylamide, methacrylamide, N-hydroxymethylacrylamide, N-(carboxyhydroxy) methacrylamide, acrylic acid, methacrylic acid, 2-vinylpyridine, 4-vinylpyridine, and a monomer corresponding to the following formula:

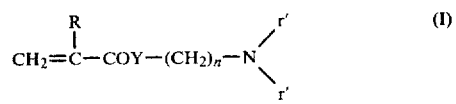

wherein:
Represents a hydrogen atom or a methyl radical,
Y represents the bivalent radical —O— or —NH—
r' represents a methyl or ethyl radical
and n is 2 or 3 and in submitting the oil thus treated to a purification operation to eliminate the ungrafted residual homopolymer.

Of the monomers of formuls (I) above there can be cited in particular: N,N-2-dimethylaminoethyl, N,N-2-diethylaminoethyl or N,N-3-dimethylaminoethyl propyl acrylates and methacrylates and N,N-2-dimethylaminoethyl, N,N-2-diethylaminoethyl or N,N-3-dimethylaminopropyl acrylamides and methacrylamides.

The invention is not limited only to the monomers listed above but also includes some of their salts such as those of acrylic or methacrylic acid obtained with an inorganic or organic base and in particular an aminoalcohol such as 2-amino-2-methyl-1-propanol or 2-amino-2-methyl-1,3-propanediol, the salts of 2-vinylpyridine or 4-vinylpyridine such as their hydrochloride or lactate and the quaternary derivatives of the compounds of formula (I) such as those obtained with dimethyl sulfate or ethyl bromide.

By the expression "cosmetic oil" as used according to this invention should be understood the oils generally used in cosmetics and being in liquid form at a temperature less than or equal to 30° C.

This expression is currently used in the cosmetic field to designate natural oils of mineral, vegetable or animal origin, on the one hand, and synthetic oils, on the other hand.

Of the various oils of the first group, those particularly preferred according to the invention are liquid petrolatum, calophyllum oil, avocado oil, jojoba oil, purcellin oil and liquid lanolin.

Of the preferred synthetic oils there can be cited in particular polyisobutylene, such as that sold by the Mishi-Yu Chemical company under the name "PARLEAM," esters of fatty alcohols having 8 to 30 carbon atoms and of alcohols having 10 to 30 carbon atoms such as that sold by the Henkel company under the tradename "CETIOL LC" (ester of fatty acids having about 12 carbon atoms and alcohols having about 16 carbon atoms), acid triglycerides having 8 to 20 carbon atoms and particularly the product sold by the Dynamit Nobel company under the tradename "MYGLIOL 812" (triglycerides of fatty acids of vegetable origin having 8 to 12 carbon atoms), or perhydrosqualene sold by the Dubois company under the name "COSBIOL."

The treatment temperature of the cosmetic oil in the presence, on the one hand, of a homopolymerizable hydrophilic monomer and, on the other hand, of the free radical generator is generally between 50° and 250° C. and preferably between 80° and 200° C.

The heating period can vary between 1 and 15 hours and preferably between 2 to 10 hours.

The initiator generating free radicals used in the process according to the invention is selected from those generally soluble in the reaction medium and which are generally used to polymerize compounds carrying polymerizable double bonds. These initiators are azo compounds such as azobisisobutyronitrile, peroxides particularly dibenzoyl peroxide, di-tert-butyl peroxide, dicumyl peroxide or peresters particularly tert-butyl peroxy 2-ethylhexanoate and tert-butyl peroxy 3,5,5-trimethylhexanoate.

According to the invention, the ratio by weight of the homopolymerizable hydrophilic monomer to the cosmetic oil is generally between 0.03:1 and 0.5:1 and preferably between 0.05:1 and 0.2:1.

The ratio by weight of the initiator generating free radicals to homopolymerizable hydrophilic monomer is generally between 0.01:1 and 0.2:1 and preferably between 0.03:1 and 0.1:1.

Although use of a solvent to perform the grafting reaction cannot be ruled out, the reaction is preferably performed according to the invention without solvent, the cosmetic oil acting both as reagent and solvent.

The purification operation takes on great importance because the homopolymer that is formed as a residual product must be eliminated from the treated oil.

This purification operation can be performed either by filtering and/or washing with a solvent selective either of the modified oil or the homopolymer formed.

The homopolymer is generally insoluble in the oils from which it can easily be separated by filtering.

Preferably, the homopolymer is first separated by filtering, then the oil is purified by one or more successive washings to obtain a modified oil totally free, on the one hand, of the starting homopolymerizable hydrophilic monomer and, on the other hand, of the homopolymer formed.

After this purification stage, the modified cosmetic oil can again be treated, if this proves to be necessary, by the same process with an identical or different homopolymerizable hydrophilic monomer which possibly makes it possible to obtain an oil exhibiting new cosmetic properties.

The process according to the invention has the merit, in relation to previously known processes for modifying oils, of being applicable to both unsaturated oils and saturated oils.

This invention also has for its object modified cosmetic oils obtained by the process as described above and the cosmetic compositions containing them.

The cosmetic compositions according to the invention are generally all cosmetic compositions containing oils. These compositions, the other ingredients they contain, their preparation and application are well known to cosmeticians. Generally, they contain at least 1% of a cosmetic oil such as obtained according to the invention.

Of the compositions according to the invention, there can be cited those that are in the form of fluid emulsions such as lotions or in the form of more consistent emulsions such as creams.

The emulsions can be the water-in-oil or oil-in-water type depending on whether the oil phase constitutes the continuous phase or dispersed phase of the invention. The oil phase of these emulsions is made up exclusively or in part of an oil modified by the process according to the invention, said phase, in the case of an oil-in-water emulsion, corresponding to about 5 to 60% by weight and preferably 20 to 40% by weight and in the case of a water-in-oil emulsion to about 20 to 70% by weight and preferably 30 to 50% by weight in relation to the total weight of the emulsion.

The water phase represents about 40 to 95% by weight and preferably 60 to 80% by weight in the case of an oil-in-water emulsion and about 30 to 80% and preferably 50 to 70% by weight in the case of a water-in-oil emulsion.

Of course, the oil phase may not be made up exclusively of an oil modified by the process according to the invention. In other words, the oil phase can be a mixture of several oils of which a part is made up of an oil modified by the process according to the invention.

Moreover, the oil phase can comprise some waxes such as carnauba wax, candellila wax, beeswax, microcrystalline wax or ozocerite.

These compositions in the form of emulsions can be moisturizing creams as, for example, sun creams, creams for the face, body or hands, or in the form of moisturizing rouges or again foundations.

According to this embodiment, the compositions according to the invention can further contain ingredients generally used in cosmetics and in particular dyes, pigments, perfumes, sun protection products, and preservative agents such as methyl parahydroxy benzoate or propyl parahydroxybenzoate, these compounds making it possible to obtain a good preservation of the emulsions.

The compositions according to the invention can also be in the form of colorless or colored makeup products for the lips.

In this case, the oil modified by the process according to the invention constitutes a part of the fatty body that generally results from the mixture of at least a wax and at least an oil.

The oils modified by the process according to the invention can be used either alone or in mixture with other modified or unmodified oils to constitute a part of the fatty body. The fatty body represents in these compositions in the form of lipstick 35 to 99.5% in relation to the total weight of the composition.

The various ingredients that can be introduced in these compositions in the form of lipstick are those conventionally used for this type of formulation.

Of these latter there can be cited in particular soluble or insoluble dyes that are generally present in a proportion between 6 and 15%, the solvents of certain dyes insoluble in fatty bodies, and particularly eosin derivatives, agents giving a pearly luster in a proportion of 2 to 20%, perfumes, sun protection agents, antioxidants and preservatives.

Of the various dyes for lipsticks there can be cited in particular: eosins and other fluorescein halogenated derivatives (bromoacids) and particularly those known by the name of D and C Red No. 21, D and C Red No. 27, D and C Orange No. 5, inorganic pigments such as oxides of iron, chromium, ultramarines (polysulfides of amino silicates), titanium dioxide, these compounds being used in a concentration of about 1 to 6%, organic pigments such as D and C Red No. 36 and D and C Orange No. 17.

Finally, the dyes can also include lacquers such as calcium lacquers of D and C Red No. 7, 21 and 27, barium lacquers of D and C Red No. 6, 9, aluminum lacquers of D and C Red No. 21, D and C Yellow No. 5 and 6, and zirconium lacquers of D and C Red No. 21 and of D and C Orange No. 5.

Of the solvents of dyes insoluble in oils there can be cited glycols, polyethylene and polypropylene glycols and monoalkanolamides.

Of the agents giving a pearly luster there can be cited in particular bismuth oxychloride, mica titanium and guanine crystals.

Of the antioxidants there can be cited in particular those of the phenol type such as propyl, octyl and dodecyl esters of gallic acid, butylated hydroxyanisole, butylated hydroxytoluene and nordihydroguaiaratic acid.

The cosmetic compositions according to the invention can also be in the form of lotions for maintenance and embellishment of the scalp and particularly compositions made up of two separate liquid phases, the first being an oil phase and the second being a water phase in which at least a cation polymer is dissolved, the oil phase being made up of an oil such as obtained by the process according to the invention or by a mixture of such oils and unmodified oils.

In a general way it is preferred to use a vegetable oil modified by the process according to the invention possibly mixed with a mineral oil and/or animal or synthetic oil.

According to this embodiment the proportion of oil modified by the process according to the invention generally varies from 5 to 100% by volume in relation to the total volume of the oil phase, the possible complement being made up of one or more animal, mineral and/or synthetic oils possibly modified by the process according to the invention.

The cation polymers that can be used in these cosmetic hair compositions constitute a class well known to cosmeticians and are described in numerous French patents and patent applications.

These cation polymers are polymers of the polyamine, polyaminoamide or quaternary polyammonium type, the amine or ammonium group being part of the polymer chain or linked to it.

The cosmetic oils modified by the process according to the invention can also enter as the main or secondary ingredient in the compositions for treatment and maintenance of nails and particularly in compositions for strengthening fragile and/or brittle nails.

For a better understanding of the invention there will now be given by way of illustration and without any limiting character, several examples of the process of modifying the properties of cosmetic oils and several examples of cosmetic compositions containing them.

EXAMPLES

Example 1

A. Process for treating liquid petrolatum

In a 4-liter reactor, provided agitation by a vibrator, a dropping funnel, a cooler, a nitrogen intake and thermometer are introduced 2 kg of liquid petrolatum (viscosity 22.9 cp) and 30 g of di-tert-butyl peroxide.

The solution is then heated at 145° C. for 40 minutes with agitation and under nitrogen.

Then 225 g of distilled N-2-vinylpyrrolidone containing 21 g of di-tert-butyl peroxide are introduced drop by drop in 3 hours.

The temperature is then kept at 145°–147° C. for an hour, then the mixture is allowed to cool to 80° C. The reaction mixture is dried at this temperature under a pressure of 20 mm of mercury for 30 min, then under 1 mm for 1 hour. It is allowed to cool at ambient temperature and then the oil is decanted from the solid fraction formed, made up of the homopolymer which makes it possible to obtain 1.8 kg of modified oil.

B. Purification of the liquid petrolatum according to Example 1

The crude modified oil is introduced in a 4-liter reactor similar to that used in Example 1.

A nitrogen current is introduced and 500 ml of distilled acetone are added.

Agitation with the vibrator is performed for 5 minutes and the phases are allowed to decant.

The oil constitutes the lower phase and is separated by decanting.

The collected oil is again introduced in the reactor to undergo a second washing therein, with 250 ml of acetone, as in the preceding washing.

After decanting, a new washing can possibly be perfomed with acetone.

The collected oil is then dried under a low vacuum (30 mm) at a temperature of about 70° C., then at 80° C. under 1 mm.

Thus 1.44 kg of purified modified oil are obtained.

The liquid petrolatum thus treated exhibits a viscosity of 24.7 cp at 25° C.

Various cosmetic oils mentioned in Table A below were treated under the same conditions as those described in example 1:

separated from the gummy residue formed, then the acetone solution is filtered to eliminate the particles in suspension.

The acetone is evaporated in a rotary evaporator under low pressure, the temperature being gradually brought to 80° C.

After filtering on fritted glass, 750 g of purified avocado oil having a viscosity of 852 cp are obtained.

Acid value: 65.7.

The oil thus obtained can be neutralized with 2-amino-2-methyl-1-propanol by adding amino alcohol to the oil under agitation. The neutralization can be either total or partial.

TABLE A

| EX | Oil | Viscosity before treatment (cp) measured at 25° C. | Monomer | Viscosity after treatment (cp) |
|---|---|---|---|---|
| 2 | Petrolatum | 22.9 | 2-hydroxyethyl monomethacrylate | 30.74 |
| 3 | " | " | Dimethylaminopropyl methacrylamide | 24.28 |
| 4 | " | " | Methacrylic acid | 29.10 |
| 5 | " | " | N,N—2-dimethylaminoethyl methacrylate | 27.02 |
| 6 | Olive | 70 | N—2-vinylpyrrolidone | 133 |
| 7 | " | " | 2-hydroxyethylmonomethacrylate | 176.4 |
| 8 | Calophyllum | 70.4 | N—2-vinylpyrrolidone | 102 |
| 9 | " | " | 2-hydroxyethyl monomethacrylate | 167.4 |
| 10 | Avocado | 68.7 | " | 194 |
| 11 | Jojoba | 36.4 | " | 82 |
| 12 | Purcellin | 11.29 | " | 13.36 |
| 13 | "Parleam" | 29.8 | " | 39.1 |
| 14 | Liquid petrolatum obtained by ex 1 | 24.7 | N—2-vinylpyrrolidone | 25.36 |
| 15 | Cosibol | 16.3 | 2-hydroxyethyl monomethacrylate | 39.9 |
| 16 | Cetiol LC | 8.77 | " | 11.88 |
| 17 | Liquid lanolin* ("Stellanol 66") | 240$^{(a)}$ | " | 353$^{(a)}$ |
| 18 | Myglyol 812 | 22.3 | " | 29.8 |

$^{(a)}$viscosity measured at 50° C.
*Density before treatment d = 0.8 at 20° C.
Density after treatment d = 0.99 at 20°C.

Example 19

Process of treating avocado oil

In a 4-liter reactor, provided with agitation by a vibrator, a dropping funnel, a cooler, nitrogen intake and a thermometer are introduced 500 g of avocado oil (viscosity 63 cp) and 7 g of di-tert-butyl peroxide. The mixture is brought to 145° C. in 40 minutes under agitation and nitrogen. There are introduced, drop by drop, in 3 hours 50 g of methacrylic acid containing 5 g of di-tert-butyl peroxide.

The reaction mixture is then brought to 145°-147° C. for 1 hour under nitrogen, then for 2 hours under pressure of 3-5 mm of Hg and then allowed to cool under vacuum.

Purification of the oil is obtained according to the example solely by filtering.

The enriched oil is then dried at 145° C. under 1 mm of Hg for 3 hours.

There are obtained 400 g of modified oil having a viscosity of 150 cp.

Acid value = 20.1.

Example 20

Process of treating avocado oil

Under the same conditions at in Example 19, 300 g of methacrylic acid are polymerized in the presence of 1 kg of avocado oil and 14 g of di-tert-butyl peroxide.

The resulting oil is then purified by triturating it with 1 liter of acetone for 30 minutes. The acetone solution is

EXAMPLES OF COMPOSITION

Example A

A water-in-oil body emulsion is prepared according to the invention by mixing the following ingredients:

| | |
|---|---|
| Modified liquid petrolatum obtained according to example 1 | 25 g |
| Preservative in sufficient amount | |
| Perfume in sufficient amount | |
| Water sufficient for | 100 g |

Example B

A treatment cream is prepared according to the invention by mixing the following ingredients:

| | |
|---|---|
| Treated liquid petrolatum obtained according to example 1 | 30 g |
| Self-emulsifying glycerol stearate sold by the Atlas Company under the tradename "ARLACEL-165" | 8 g |
| Preservative in sufficient amount | |
| Perfume in sufficient amount | |
| Sterile demineralized water sufficient for | 100 g |

Example C

A foundation is prepared according to the invention in the form of a water-in-oil emulsion by mixing the following ingredients:

| Sorbitan sesquimonoleate | 3 g |
| --- | --- |
| Sorbitan trioleate polyoxyethylenated with 20 moles of ethylene oxide | 3 g |
| Modified oil obtained according to example 11 | 16 g |
| Beeswax | 1 g |
| Ozocerite | 1 g |
| Isopropyl myristate | 5 g |
| Glycerin | 5 g |
| Pigments and dyes in sufficient amount | |
| Perfume in sufficient amount | |
| Sterile demineralized water sufficient for | 100 g |

Example D

An eye shadow is prepared according to the invention in the form of an emulsion by mixing the following ingredients:

| Stearic acid | 2.5 g |
| --- | --- |
| Sorbitan monostearate polyoxyethylated with 40 to 60 moles of ethylene oxide | 0.5 g |
| Modified oil obtained according to example 14 | 10 g |
| Sorbitol | 5 g |
| Triethanolamine | 1 g |
| Pigments and dyes in sufficient amount | |
| Titanium dioxide | 3 g |
| Preservative in sufficient amount | |
| Perfume in sufficient amount | |
| Sterile demineralized water sufficient for | 100 g |

Example E

A body lotion is prepared according to the invention in the form of an oil-in-water emulsion by mixing the following ingredients:

| Modified oil obtained according to example 14 | 15 g |
| --- | --- |
| Paraffin oil | 35 g |
| Preservative in sufficient amount | |
| Perfume in sufficient amount | |
| Demineralized water sufficient for | 100 g |

Example F

Oil and water phases having the following compositions are prepared:

| Oil phase | |
| --- | --- |
| Avocado oil modified according to example 10 | 10 cc |
| Antioxidant in sufficient amount | |
| Perfume in sufficient amount | |
| Dye in sufficient amount | |
| Colza oil sufficient for | 100 cc |
| Water phase | |
| Cation polymer made up of groups of the formula: | |

$$\left[ \begin{array}{cc} CH_3 & CH_3 \\ | & | \\ N^{\oplus}-(CH_2)_3-N^{\oplus}-(CH_2)_6 \\ | & | \\ CH_3 \ Cl^{\ominus} & CH_3 \ Cl^{\ominus} \end{array} \right]$$

| described in French patents No 2,270,846 and 2,33,012 | 1.5 g |
| --- | --- |
| "JR 400" polymer of hydroxyethylcellulose and epichlorohydrin quaternized with trimethylamine with a viscosity of 400 cp sold by the Union Carbide Company | 1 g (M.A.) |
| Preservative in sufficient amount | |
| Dye in sufficient amount | |
| Water sufficient for | 100 cc |

The composition in two phases is obtained by juxtaposition of 4 cc of the water phase with 16 cc of the oil phase.

After agitation, the composition is applied to dried or sensitized hair. After an exposure time of 5 minutes to 4 hours but preferably 15 minutes, the hair is rinsed, then shampooed.

The wet hair easily untangles. The dry hair is soft, full-bodied and shiny.

Example G

There are mixed 18 cc of oil phase and 2 cc of water phase having the following composition:

| Oil phase | |
| --- | --- |
| Olive oil modified according to example 7 | 7 cc |
| Antioxidant in sufficient amount | |
| Perfume in sufficient amount | |
| Dye in sufficient amount | |
| Soybean oil sufficient for | 100 cc |
| Water phase | |
| "Merquat 100" homopolymer of dimethyldiollyl ammonium chloride of a molecular weight less than 100,000 sold by Merck & Co | 3 g (M.A.) |
| "Cartartine F4" copolymer of adipic acid/dimethylaminohydroxypropyl diethyline triamine sold by the Sandoz Company | 5 g (M.A.) |
| Preservative in sufficient amount | |
| Dye in sufficient amount | |
| Water sufficient for | 100 cc |

Example H

There are mixed 10 cc of oil phase and 10 cc of water phase having the following compositions:

| Oil phase | |
| --- | --- |
| Jojoba oil modified according to example 11 | 20 cc |
| antioxidant in sufficient amount | |
| Perfume in sufficient amount | |
| Dye in sufficient amount | |
| Sesame oil sufficient for | 100 cc |
| Water phase | |
| Identical with that of example G. | |

Example I

A preshampoo composition is prepared according to the invention by mixing the following ingredients:

| Modified avocado oil obtained according to example 10 | 98.7 g |
| --- | --- |
| Perfume | 0.7 g |
| Dye | 0.1 g |
| Butylhydroxytoluene | 0.5 g |

After the composition is allowed to act for 15 min, shampooing is performed. The hair is soft and shiny.

Example J

A lipstick is prepared according to the invention by mixing the following ingredients:

| Microcrystalline wax | 11 g |
| --- | --- |
| Polyvinyl laurate | 20 g |
| 1-docosanoyl (2-ethyl) 3-hexyloxy-2-propanol | 20 g |
| Liquid lanolin | 7 g |
| Castor oil | 6 g |

| -continued | |
|---|---|
| Sesame oil | 7 g |
| Modified oil (liquid lanolin) obtained according to example 17 | 7 g |
| Acetoglyceride | 9 g |
| Liquid petrolatum | 5 g |
| Oleic alcohol | 5 g |
| Butylhydroxytoluene | 0.2 g |
| Polyethylene wax | 2.8 g |
| Black iron oxide | 0.2 g |
| Titanium oxide | 1.1 g |
| Aluminum lacquer of F.D. and C Yellow 5 | 2.4 g |
| Calcium lacquer of D and C Red 7 | 1.45 g |
| Aluminum lacquer of D and R Red 3 | 5.3 g |
| D and C Red 21 | 2 g |
| Perfume | 0.8 g |

Example K

A lipstick is prepared according to the invention by mixing the following ingredients:

| | |
|---|---|
| Hard microcrystalline was | 10 g |
| Isopropyl lanolate | 6 g |
| Lanolin alcohol | 6 g |
| Soft microcrystalline wax | 10 g |
| Myristyl lactate | 8 g |
| Liquid lanolin | 8 g |
| Polybutene | 20 g |
| Sesame oil | 10 g |
| Castor oil | 10 g |
| Oleic alcohol | 7.9 g |
| Modified liquid petrolatum obtained according to example 3 | 2 g |
| Butylhydroxytoluene | 0.1 g |
| Brown iron oxide | 2.7 g |
| Calcium lacquer D and C of Red 7 | 0.18 g |
| D and C Red 8 (sodium salt) | 1.26 g |
| Aluminum lacquer of D and C Red 3 | 5.10 g |
| Titanium oxide | 1.10 g |
| D and C Red 21 | 2 g |
| Perfume | 0.6 g |

Example L

A lip gloss is prepared according to the invention by mixing the following ingredients:

| | |
|---|---|
| Vinyl acetate/allyl stearate copolymer 35/65 | 5 g |
| Polyvinyl laurate | 20 g |
| 1-docosanoyl (2-ethyl) 3-hexyloxy-2-propanol | 20 g |
| Polyethylene wax | 15 g |
| Mineral oil | 10 g |
| Sesame oil | 2 g |
| Oleic alcohol | 3 g |
| Butylhydroxytoluene | 0.1 g |
| Butyl para-hydroxybenzoate | 0.2 g |
| Polyethylene wax | 2 g |
| Liquid lanolin | 11.7 g |
| Modified oil (liquid lanolin) obtained according to example 17 | 7 g |
| Titanium oxide | 0.1 g |
| D and C Red 36 | 1.1 g |
| D and C Red 30 | 0.2 g |
| D and C Red 21 | 0.5 g |
| Perfume | 0.2 g |

Example M

A rouge in the form of a compact powder is prepared according to the invention by mixing the following ingredients:

| | |
|---|---|
| Talc | 41.64 g |

| -continued | |
|---|---|
| Starch | 10 g |
| Zinc stearate | 2 g |
| Bismuth oxychloride | 10 g |
| Castor oil | 0.7 g |
| Modified liquid petrolatum obtained according to example 4 | 3.5 g |
| Isopropyl myristate | 0.5 g |
| Oleic alcohol | 0.6 g |
| Phytosterol | 0.3 g |
| Polypeptide oleate | 0.3 g |
| Butyl hydroxyanisole | 0.01 g |
| Magnesium carbonate | 0.55 g |
| Magnaese violet | 7 g |
| Iron oxide | 2 g |
| Mica titanium | 20 g |
| D and C Red 21 | 0.5 g |
| Perfume | 0.4 g |

We claim:

1. A process for modifying the properties of an unsaturated or saturated cosmetic oil by grafting so as to reduce its volatility and to improve its emulsifying power, said process comprising heating in the absence of a solvent and under an inert atmosphere, a natural or synthetic cosmetic oil with a homopolymerisable and hydrophilic monomer in the presence of an initiator generating free radicals, said monomer being selected from the group consisting of N-vinylpyrrolidone, 2-hydroxymethyl acrylate, 2-hydroxymethyl methacrylate, acrylamide, methacrylamide, N-hydroxymethylacrylamide, N-(carboxyhydroxy)methacrylamide, acrylic acid, methacrylic acid, 2-vinylpyridine, 4-vinylpyridene and a monomer having the formula

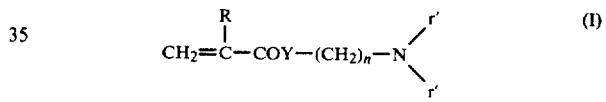

wherein
R represents hydrogen or methyl,
Y represents —O— or —NH—,
r' represents methyl or ethyl and
n is 2 or 3, and
purifying the resulting modified cosmetic oil so as to remove any insoluble nongrafted homopolymer.

2. The process of claim 1 wherein said cosmetic oil is heated at a temperature between 50° and 250° C.

3. The process of claim 1 wherein said cosmetic oil is heated at a temperature between 80° and 200° C.

4. The process of claim 1 wherein said heating is carried out for a period of time ranging from 1 to 15 hours.

5. The process of claim 1 wherein said heating is carried out for a period of time ranging from 2 to 10 hours.

6. The process of claim 1 wherein said cosmetic oil is selected from the group consisting of liquid petrolatum, olive oil, jojoba oil, purcellin oil and liquid lanolin.

7. The process of claim 1 wherein said cosmetic oil is selected from the group consisting of polyisobutylene, an ester of a fatty acid having 8–30 carbon atoms and an alcohol having 10–30 carbon atoms, an acid triglyceride having 8–21 carbon atoms and perhydrosqualene.

8. The process of claim 1 wherein said homopolymerizable and hydrophilic monomer is selected from the group consisting of a salt of acrylic or methacrylic acid with an inorganic or organic base, a salt of 2-vinylpyridine or 4-vinylpyridine with hydrochloric acid or lactic acid, and a quaternary ammonium derivative of a compound of the formula (I).

9. The process of claim 1 wherein said initiator generating free radicals is selected from the group consisting of azobisisobutyronitrile, dibenzoyl peroxide, di-tert.-butyl peroxide, dicumyl peroxide, tert.-butyl peroxy 2-ethylhexanoate and tert.-butyl peroxy 3,5,5-trimetylhexanoate.

10. The process of claim 1 wherein the weight ratio of said homopolymerizable and hydrophilic monomer to said cosmetic oil ranges from 0.03:1 to 0.5:1.

11. The process of claim 1 wherein the weight ratio of said homopolymerizable and hydrophilic monomer to said cosmetic oil ranges from 0.05:1 to 0.2:1.

12. The process of claim 1 wherein the weight ratio of said initiator generating free radicals to said homopolymerizable and hydrophilic monomer ranges between 0.01:1 to 0.2:1.

13. The process of claim 1 wherein the weight ratio of said initiator generating free radicals to said homopolymerizable and hydrophilic monomer ranges between 0.3:1 to 0.1:1.

14. A cosmetic oil modified by grafting and obtained by the process of claim 1.

* * * * *